United States Patent [19]

Bhaskaran et al.

[11] Patent Number: 5,266,702

[45] Date of Patent: Nov. 30, 1993

[54] 1,3-OXAZOLINE COMPOUNDS USEFUL AS ANIONIC INITIATORS SUITABLE FOR POLYMERIZATION OF VINYL POLYMERS

[75] Inventors: Durairaj Bhaskaran; Pradeep K. Dhal; Sanjay P. Kashikar; Ratnaprabha S. Khisti; Babanrao M. Shinde; Swaminathan Sivaram, all of Maharashtra, India

[73] Assignee: Council of Scientific & Industrial Research, New Delhi, India

[21] Appl. No.: 585,683

[22] Filed: Sep. 19, 1990

[51] Int. Cl.$^5$ .............................................. C07D 263/32
[52] U.S. Cl. .................................... 548/235; 546/145; 558/443; 560/105
[58] Field of Search ........................................... 548/235

[56] References Cited

U.S. PATENT DOCUMENTS 4,391,814  7/1983  Vorbruggen ........................ 548/239
4,574,157  3/1986  Homann ............................... 548/239

*Primary Examiner*—C. Warren Ivy
*Assistant Examiner*—James H. Turnipseed

*Attorney, Agent, or Firm*—Ladas & Parry

[57] ABSTRACT

Disclosed are reactive anionic initiators of the general formula [ArCHR$_1$R$_2$N(R$_3$R$_4$R$_5$R$_6$] wherein Ar=phenyl, substituted phenyl, or a heterocyclic compound, R$_1$=R$_2$=H, ester, cyano, alkyl, aryl, 1,3-oxazoline, N,N-dimethyl amide and other similar alpha activating groups, or combination of them, or one of R$_1$ or R$_2$ together with Ar, where Ar is a phenyl or substituted phenyl, is a nitrogen atom containing heterocyclic compound and the other being a nitrile group, R$_3$, R$_4$, R$_5$ and R$_6$ may be same or different and represent substituted alkyl, cycloalkyl, arylalkyl or aryl or to of the R$_3$, R$_4$, R$_5$ and R$_6$ together with nitrogen atom form a heterocycle with the condition that the sum of all carbon atoms of all R$_3$, R$_4$, R$_5$ and R$_6$ is from 12 to 50 and no more than one of the R$_3$, R$_4$, R$_5$ and R$_6$ is an aryl derivative. The initiators which are in the form of solids or liquids are insoluble and can be incorporated which enable the synthesis of a wide range of polymers with functional groups. These initiators are useful for polymerizing very reactive vinyl monomers such as nitrile bearing vinyl compounds.

4 Claims, No Drawings

1,3-OXAZOLINE COMPOUNDS USEFUL AS ANIONIC INITIATORS SUITABLE FOR POLYMERIZATION OF VINYL POLYMERS

This invention relates to novel reactive anionic initiators and a process for preparing the same. The initiators are particularly useful for the polymerization of vinyl monomers.

The invention relates to the preparation of metal-free carbanionic initiators bearing functional groups. The functional groups may be cyanide, ester, 1,3-oxozoline, amide etc. The initiators prepared can also be used as a functional intermediates in organic synthesis. These initiators can also be used for the polymerization of vinyl monomers with controlled structure and molecular weight. In particular, they are useful for polymerising very reactive vinyl monomers such as nitrile bearing vinyl compounds.

Conventional methods of preparation of carbanion initiators consists of reacting alkali metals such as Li, Na and alkaline earth metals such as Mg and Zn with alkyl or aryl halides (viz. chloride, bromide and iodide). (M. Morton, Anionic Polymerization, Principles and Practice, Academic Press, New York, 1983).

Initiators prepared by the above conventional method can be used for polymerization of vinyl compounds. However, adequate control on polymerisation rate and structures for alpha activated vinyl monomers are achievable only at temperature below −50° C. This is due to the extremely high reactivity of the initiators (P. Rempp, E. Franta and J-E. Herz, Advances in Polymer Science, Volume 86, p. 147, 1988).

Conventional process of initiator synthesis involves reaction or organic halides with metals, which is a biphasic solid-liquid reaction. This heterogeneous nature of the reaction needs longer time and higher temperature for quantitative yield. Furthermore, scope is limited with respect to control of reactivity of the initiators.

The existing methods for synthesis of carbanionic initiators cannot provide control over their reactivities. Hence their use in polymerization of vinyl monomers with a wide range of reactivities are limited.

The major disadvantages of the initiators prepared by the above said processes are:

a) The initiators are unstable at temperature above −20° C. and thus need storage at low temperature under inert atmosphere.

b) The metallic counterions being highly polar do not provide wider choice of using common organic solvents.

c) The metallic counterions which will remain with the polymer are detrimental to the properties of the polymer and need cumbersome procedures of purification.

d) The initiators lack structural diversity and are therefore not useful for introducing functional groups in the polymer.

e) Metal containing initiators thus prepared do not enable adequate control on molecular weight and molecular weight distribution of the polymers obtained from highly reactive vinyl monomers such as those bearing nitrile groups, ester etc.

Carbanions can also be prepared from organic compounds bearing labile hydrogens (acidic hydrogen) by deprotonation using a strong base such as sodium hydroxide, sodium hydride, n-butyl-lithium etc. However, these metal containing carbanions are also beset with the same drawbacks described above.

More recently carbanion salts useful as initiators for polymerization of acrylic and methacrylic acid esters have been prepared by reacting organic compounds containing labile (acidic) hydrogen with a base such as quaternary ammonium hydroxide (M. T. Reetz, T. Knauf, U. Minet and C. Bingel, Angew Chem. Intl. Ed. Engl., Vol. 27, No. 10, p. 1988). However, the organic compounds described herein are extensively branched, contain only one tertiary hydrogen, the other substituents being strong electron withdrawing like cyano, nitro, ester etc. and thus form highly stabilized carbanions. These compounds have been known in the literature to be very acidic (pkA's being less than 10–11, measured in water at 25° C.) (J. R. Jones, Ionization of Carbon Acids, Academic Press, New York, 1973, p.63) and thus easy to form salts with bases such as quaternary ammonium hydroxides (A Brand Strom, U. Junggren Acta. Chem. Scand, Vol.25, p.1469, 1971).

However, the prior art does not disclose the preparation of stable carbanions from simple organic compounds containing primary and secondary hydrogen atoms and their utility as polymerization initiators. These carbanions have been reported in the literature to lead to complicated side reactions such as proton transfer, undesired condensations between reacting species and competing 1,2 and 1,4 additions with unsaturated vinyl monomers containing α-activating groups like carbonyl, nitrile etc. Carbanions from less acidic organic compounds can be generated using strong bases such as n-BuLi, lithium diisopropylamide etc. at a temperature of −50° C. or below. The carbanions so generated are also stable only at these low temperatures (J. C. Stowell, Carbanions in Organic Synthesis, John Wiley and Sons, New York, 1979, p.144).

For controlled polymerization of very reactive monomers such as acrylonitrile, methacrylonitrile etc. it is desirable to have more nucleophilic carbanionic initiators whose reactivity matches closely that of the propagating carbanion. This can be achieved only by tailoring the carbanion stability through choice of appropriate substituent.

The main object of the present invention is to provide a generalized method of generating carbanions from less acidic organic compounds bearing secondary and primary hydrogen atoms without the attendant side reactions and complications reported in the prior art for the synthesis of such carbanions. It is also an objective to prepare these carbanions with metal free counter cations. Since the reactivity of carbanions can be tailored by suitable α-functional groups, these initiators could provide a means of introducing functional groups as head groups in oligomers and polymers.

Accordingly, the present invention provides for novel reactive anionic initiators of the general formula [ArCHR$_1$R$_2$NR$_3$R$_4$R$_5$R$_6$], wherein Ar=phenyl, substituted phenyl or a heterocyclic compound, R$_1$=R$_2$=H, ester, cyano, alkyl, aryl, 1,3-oxazoline, N,N-dimethyl amide and other similar alpha activating groups or combination of them; or one of R$_1$ and R$_2$ together with Ar, where Ar is phenyl or substituted phenyl, is a nitrogen atom containing heterocyclic compound and other being a nitrile group, R$_3$, R$_4$, R$_5$, and R$_6$ may be same or different and are each hydrocarbyl groups of 3 to 16 carbon atoms and represent substituted aklyl, cycloalkyl, arylalkyl or aryl or two of the R$_3$, R$_4$, R$_5$, and R$_6$ together with nitrogen atom form a heterocyclic ring of 5 to 7 atoms with the condition that the sum of all carbon atoms of all $R_3$, $R_4$, $R_5$, and $R_6$ is from 12 to 50 and no more than one of the $R_3$, $R_4$, $R_5$, and $R_6$ is an aryl derivative. Typically such alkyl groups have from 3 to 16 carbon atoms, cycloalkyl groups have from 5 to 8 carbon atoms, arylalkyl groups have 7 to 10 carbon atoms and aryl groups have 6 carbon atoms. The process for preparing the said initiators comprises reacting an organic compound containing labile hydrogen and having a general formula $ArCHR_1R_2$ where $R_1$ or $R_2$ are selected from COOEt, CN, Ph, alkyl, 1,3-oxazoline or N,N-dimethyl amide or combination of them, Ar=phenyl, substituted phenyl or a heterocyclic compound or one of the $R_1$ and $R_2$ together with Ar, where Ar is a phenyl or substituted phenyl, is a heterocyclic compound and other being a nitrile group such as 2-benzyl-1,3-oxazoline, diethyl-phenylmalonate, methylphenylacetate, diethylmalonate, 1-cyano-dihydroisoquinoline, with a base generally soluble in organic solvents such a tetra-n-butyl ammonium hydroxide, on benzyl tri-n-butyl ammonium hydroxide in an inert atmosphere at a temperature range of +50° to +90° C.

The inert atmosphere may be achieved using purified dry nitrogen or argon gas and the like.

The reaction may preferably be effected in the presence of organic solvents such as benzene, toluene, tetrahydrofuran.

The reaction mixture may be agitated and may be held at constant temperature for a minimum period of 3 hours. The solvent may be distilled out to give initiator which can be isolated either as an oil or as solid and stored under suitable conditions.

The invention is described with reference to the following examples which should not be construed to limit the scope of the invention.

EXAMPLE 1

Preparation of Initiator from 2-Benzyl-1,3-oxazoline:

To a three necked 100 mL round bottom flask fitted with a thermometer, nitrogen inlet, rubber septum and magnetic needle, 2.5 mmol of 2-benzyl-1,3-oxazoline and 50 mL dry tetrahydrofuran (THF) were added with a hypodermic syringe under an atmosphere of dry nitrogen. While stirring, 2.5 mmol of tetrabutylammonium hydroxide (20% solution in toluene/methanol) was added. The reaction mixture was stirred for ½ hour at room temperature and the temperature was slowly raised to +50° C. and maintained for 3 hours at that temperature. Appearance of a deep red colored solution is indicative of the carbanion formation. The reaction mixture was cooled to room temperature, the solvent was evaporated under vacuum and the product was dried at 40° C. under vacuum. The carbanion salt (tetra-n-butyl ammonium 2-benzyl-1,3-oxazoline) thus obtained is a deep red oily residue which has desired spectral features.

EXAMPLE 2

Preparation of Initiator from Diethylphenylmalonate:

To a three necked 100 mL round bottom flask fitted with a argon inlet, dropping funnel, distillation unit and magnetic needle, was added 7.7 mmoles of tetrabutylammonium hydroxide (20% solution in toluene/methanol) in 40 mL of dry toluene and heated to +75° C. to +85° C. Diethylphenylmalonate (9.3 mmoles) was slowly added. Simultaneously an azeotrope of toluene-water was distilled out slowly over a period of 3 hours. After all toluene had distilled over, the flask was cooled to room temperature slowly. A solid product separated out, which was repeatedly washed with dry hexane. The initiator (tetra-n-butyl ammonium diethylphenyl malonate) thus formed was dried in vacuum and stored at room temperature under nitrogen or argon.

EXAMPLE 3

Preparation of Initiator from Methylphenylacetate:

In a similar apparatus as described in example 2, 7.7 mmoles of tetrabutylammonium hydroxide (20% solution in toluene/methanol) in 40 ml of dry toluene was taken and heated to +75° C. to +85° C. Methylphenylacetate (9.0 mmoles) was slowly added. Simultaneously an azeotrope of toluene-water was distilled out slowly over a period of 3 hours. After all toluene had distilled over, the flask was cooled to room temperature slowly. A solid product separated out, which was repeatedly washed with dry hexane. The initiator (tetra-n-butyl ammonium methylphenylacetate) thus formed was dried in vacuum and stored at room temperature under nitrogen or argon.

EXAMPLE 4

Preparation of Initiator from Ethylcyanoacetate

In a similar apparatus as described in example 2, 7.7 mmoles of tetra-n-butyl ammonium hydroxide (20% solution in toluene/methanol) in 40 ml of dry toluene and heated to +75° C. to +85° C. Ethylcyanoacetate (9.4 mmoles) was slowly added. Simultaneously an azeotrope of toluene-water was distilled out slowly over a period of 3 hours. After all toluene had distilled over, the flask was cooled to room temperature slowly. A solid product separated out, which was repeatedly washed with dry hexane. The initiator (tetra-n-butyl ammonium ethylcyanoacetate) thus formed was dried in vacuum and stored at room temperature under nitrogen or argon.

EXAMPLE 5

Preparation of Initiator from 2-Methyl-1,3-oxazoline

In a similar experimental set described in example 1, 10 mmoles of 2-methyl-1,3-oxazoline and 50 ml dry tetrahydrofuran (THF) were added with hypodermic syringe under an atmosphere of dry $N_2$. While stirring 10 mmoles of tetra-n-butyl ammonium hydroxide (20% solution in toluene/methanol) was added. The reaction mixture was stirred for ½ hour at room temperature and the temperature was slowly raised to 50° C. and maintained for 8 hours at that temperature. Appearance of faint yellow coloured solution is indicative of the carbanion formation. The reaction mixture was cooled to room temperature, the solvent was evaporated under vacuum and the product was dried at 40° C. under vacuum. The carbanion salt (tetra-n-butyl ammonium 2-methyl-1,3-oxazoline) obtained is a faint yellow oily residue which had the desired spectral features.

EXAMPLE 6

Preparation of Initiator from N-benzoxy-2-cyano-dihydroisoquinoline

A similar experimental apparatus was set up as described in example 1, mmoles of N-benzoxy-2-cyano-dihydroisoquinoline and 50 ml dry tetrahydrofuran (THF) were added with a hypodermic syringe under an atmosphere of dry nitrogen. While stirring 5 mmoles of tetra-n-butyl ammonium hydroxide (20% solution in toluene/methanol) was added. The reaction mixture was stirred for ½ hour at room temperature and the temperature was slowly raised to +50° C. and maintained for 3 hours at that temperature. Appearance of a deep red coloured solution in indicative of the carbanion formation. The reaction mixture was cooled to room temperature, the solvent was evaporated under vacuum and the product was dried at +40° C. under vacuum. The carbanion salt (tetra-n-butyl ammonium-N-benzoxy-2-cyano-dihydro isoquinoline obtained is a deep red coloured oily residue.

The main advantages of the present invention are:

a) The initiators can be prepared over a temperature range of +50° C. to +90° C.

b) The initiators which are in the form of solids or liquids are isolable and can be conveniently stored at ambient temperature. The initiators can also be prepared in two phase systems containing of an organic and an aqueous phase.

c) They are free from metal ions.

d) Several types of functional groups can be incorporated by using a range of readily available organic compounds as starting materials. These enable the synthesis of a wide range of polymers with functional groups.

e) It is possible to vary the reactivity of the initiators over a wide range by the appropriate choice of substituents in the starting material.

We claim:

1. A reactive anion initiator of the formula:

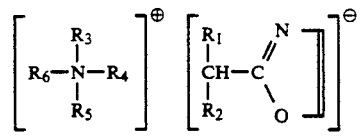

wherein $R_1$ is hydrogen and $R_2$ is selected from the group consisting of hydrogen, $COOC_2H_5$, cyano, alkyl, aryl or 1,3 oxazoline and $R_3$, $R_4$, $R_5$ and $R_6$ may be the same or different and are each hydrocarbyl of 3 to 16 carbon atoms, with the conditions that the sum of all carbon atoms of $R_3$, $R_4$, $R_5$ and $R_6$ is from 12 to 50 and that no more than one of $R_3$, $R_4$, $R_5$ and $R_6$ is an aryl derivative.

2. An initiator as claimed in claim 1 which is a carbanion salt: tetra-n-butyl ammonium 2-benzyl 1,3-oxazoline.

3. A reactive anion initiator of the formula

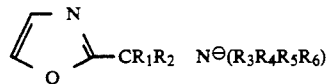

wherein $R_1$ is hydrogen and $R_2$ is hydrogen, aryl or a 1,3 oxazoline group and $R_3$, $R_4$, $R_5$ and $R_6$ may be the same or different and are each hydrocarbyl of 3 to 16 carbon atoms with the conditions that the sum of all carbon atoms of all $R_3$, $R_4$, $R_5$ and $R_6$ is from 12 to 50 and that no more than one of $R_3$, $R_4$, $R_5$ and $R_6$ is an aryl group.

4. An initiator as claimed in claim 3 which is a carbanion salt: tetra-n-butyl ammonium 2-methyl-1,3-oxazoline.

* * * * *

UNITED STATES PATENT AND TRADEMARK OFFICE
CERTIFICATE OF CORRECTION

PATENT NO. : 5,266,702
DATED : November 30, 1993
INVENTOR(S) : Durairaj BHASKARAN, et al.

It is certified that error appears in the above-identified patent and that said Letters Patent is hereby corrected as shown below:

Column 6, lines 20-25
Claim 3, line 2, should be

-- 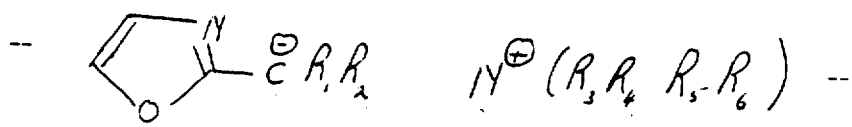 --

Signed and Sealed this

Twelfth Day of July, 1994

Attest:

BRUCE LEHMAN

Attesting Officer        Commissioner of Patents and Trademarks